United States Patent
Haschke et al.

(10) Patent No.: US 9,943,097 B2
(45) Date of Patent: Apr. 17, 2018

(54) NUTRITIONAL COMPOSITION

(75) Inventors: Ferdinand Haschke, La Tour-de-Peilz (CH); Corinne Renee Magliola, Pully (CH); Philippe Steenhout, La Tour-de-Peilz (CH)

(73) Assignee: Nestec S.A., Vevey (CH)

( * ) Notice: Subject to any disclaimer, the term of this patent is extended or adjusted under 35 U.S.C. 154(b) by 1004 days.

(21) Appl. No.: 12/519,043

(22) PCT Filed: Dec. 10, 2007

(86) PCT No.: PCT/EP2007/063622
§ 371 (c)(1),
(2), (4) Date: Jun. 12, 2009

(87) PCT Pub. No.: WO2008/071667
PCT Pub. Date: Jun. 19, 2008

(65) Prior Publication Data
US 2010/0092610 A1    Apr. 15, 2010

(30) Foreign Application Priority Data
Dec. 15, 2006   (EP) .................................... 06126282

(51) Int. Cl.
*A23C 9/20*     (2006.01)
*A23L 33/19*    (2016.01)
*A23L 33/00*    (2016.01)
*A23L 33/12*    (2016.01)

(52) U.S. Cl.
CPC .............. *A23L 33/19* (2016.08); *A23L 33/12* (2016.08); *A23L 33/40* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 6,787,158 B1 | 9/2004 | Erdmann et al. | |
| 2003/0124237 A1 | 7/2003 | Kuhlman et al. | |
| 2005/0256031 A1* | 11/2005 | Hageman et al. | 514/2 |

FOREIGN PATENT DOCUMENTS

| | | | |
|---|---|---|---|
| EP | 0880902 A1 | | 12/1998 |
| WO | 01/22837 A1 | | 4/2001 |
| WO | WO 01/22837 | * | 4/2001 |
| WO | WO 2004/112508 | | 12/2004 |
| WO | WO 2006/057551 | | 6/2006 |
| WO | WO 2006/069918 | | 7/2006 |
| WO | WO 2007/004878 | | 1/2007 |

OTHER PUBLICATIONS

Owen et al. "Effect of Infant Feeding on the Risk of Obesity Across the Life course: A Quantitative Review of Published Evidence" in Pediatrics, 115, 2005, p. 1367-1377.*
Gibson et al. "Ratios of linoleic acid to alpha-linolenic acid in formulas for term infants." J. Pediatr. 1994: 125(5 Pt 2): S48-56—Abstract Only.*
Makrides et al., "A randomized trial of different ratios of linoleic to α-linolenic acid in the diet of term infants effects on visual function and growth," Am J Clin Nutr, 2001, 71, p. 120-129.*
von Kries et al., "Breast feeding and obesity: cross sectional study," BMJ, vol. 319, Jul. 17, 1999, p. 147-150.*
International Search Report for International Application No. PCT/EP2007/063622 dated Feb. 20, 2008.
Written Opinion for International Application No. PCT/EP2007/063622 dated Feb. 20, 2008.
H. Demmelmair, et al., "Long-term consequences of early nutrition," Early Human Development, vol. 82, No. 8, Aug. 2006, pp. 567-574.
S. Fomon, et al., "What is the safe protein-energy ration for infant formulas?" American Journal of Clinical Nutrition, vol. 62, 1995, pp. 358-363.
Rudiger vonKries, et al., "Breast feeding and obesity: cross sectional study," Papers BMJ, vol. 319, Jul. 17, 1990, pp. 147-150.
Gunnarsdottir et al., "Relationship between growth and feeding in infancy and body mass index at the age of 6 years," International Journal of Obesity (2003), vol. 27, pp. 1523-1527.

* cited by examiner

*Primary Examiner* — Elizabeth Gwartney
(74) *Attorney, Agent, or Firm* — K&L Gates LLP

(57) ABSTRACT

A nutritional composition for infants at risk of developing obesity later in life comprises a protein source, a lipid source and a carbohydrate source and has a protein content of less than 1.8 g/100 kcal and an energy density of less than 650 kcal/liter.

15 Claims, No Drawings

NUTRITIONAL COMPOSITION

This invention relates to a nutritional composition, more specifically to a nutritional composition designed for infants deemed to be at risk of developing obesity later in life.

Mother's milk is recommended for all infants. However, in some cases breast feeding is inadequate or unsuccessful or inadvisable for medical reasons or the mother chooses not to breast feed either at all or for a period of more than a few weeks. Infant formulas have been developed for these situations.

The prevalence of obesity and overweight in adults, children and adolescents has increased rapidly over the past 30 years in the United States and globally and continues to rise. Overweight and obesity are classically defined based on the percentage of body fat or, more recently, the body mass index or BMI. The BMI is defined as the ratio of weight in Kg divided by the height in meters, squared. As overweight and obesity become more prevalent in all age groups, it is inevitable that the number of women giving birth who are also overweight or obese will increase. It is known that overweight and obese women who become pregnant have a greater risk of developing gestational diabetes. Maternal hyperglycaemia may lead to infants with increased body size and fat mass and such infants are themselves prone to develop obesity and diabetes later in childhood or in adult life. Moreover, recent research has suggested that obese women who themselves have normal glucose tolerance give birth to infants with a higher fat mass than those born to women who are not obese.

An increasing weight of scientific evidence suggests that infants born to overweight and obese mothers have a greater risk of becoming overweight or obese later in life than infants born to mothers who are not overweight or obese. This predisposition appears to be higher if both parents are affected. Childhood overweight and obesity currently affects 18 million children under age 5 worldwide. Almost 30% of US children and adolescents and between 10 and 30% of European children are overweight or obese.

There is, therefore, clearly a need for a nutritional composition specifically designed to address the nutritional needs of these at risk infants whilst reducing their risk of developing obesity later in life.

SUMMARY OF THE INVENTION

Accordingly, the present invention provides a nutritional composition for infants at risk of developing obesity later in life comprising a protein source, a lipid source and a carbohydrate source and having a protein content of less than 1.8 g/100 kcal and an energy density of less than 650 kcal/liter.

The invention also extends to the use of a protein source, a lipid source and a carbohydrate source for the preparation of a nutritional composition having a protein content of less than 1.8 g/100 kcal and an energy density of less than 650 kcal/liter for administration to an infant at risk of developing obesity later in life in the first year of life of the infant so as to reduce that risk.

The invention further extends to a method of reducing the possibility that an infant at risk of developing obesity later in life will develop obesity comprising feeding to the at risk infant in the first year of its life a nutritional composition comprising a protein source, a lipid source and a carbohydrate source and having a protein content of less than 1.8 g/100 kcal and an energy density of less than 650 kcal/liter.

Preferably at least 20% by weight of the protein source is casein, more preferably at least 30%.

Preferably, the ratio of linoleic acid (C18:2n–6): α-linolenic acid (C18:3n–3) in the lipid source is less than 7:1. Further, the ratio of arachidonic acid (C20:4n–6):docosahexaenoic acid (C22:6n–3) in the lipid source is preferably between 2:1 and 1.1.

Although obesity in childhood and adolescence is certainly increasing to the point where it is starting to be a cause of serious concern to healthcare professionals, there are clearly many contributory factors, nutritional, environmental and inherited. It is recognized that the likelihood of developing a nutritional product which is effective in reducing this risk in the infant population at large is remote. However, in the specific case of infants born to overweight and obese mothers, the present inventors believe that it may be possible to reduce the risk of future obesity by feeding the at risk infant from the age of about three months with a nutritional composition according to the invention. In other words, it is thought that feeding the at risk infant with a nutritional composition according to the invention from the age of about three months will result in the growth rate of the infant more closely approximating to the normal growth rate of a breast fed infant of the same age.

As research into the composition of human milk continues, increasing attention is being paid to the extent to which its composition changes over the period of lactation. These changes are particularly pronounced as regards protein quality and quantity. Dietary protein provides the essential amino acids necessary for protein synthesis and growth. Nutritional compositions to be fed to infants are usually based on cows' milk but the amino acid profile of cows' milk is noticeably different from that of human milk which, in addition, has the lowest protein concentration found in any mammalian milk. In the past, in order to supply enough of the essential amino acids, infant formulas based on cows' milk had to have a protein content significantly higher than that of the human milk. More recently, it has been realised that total protein quantity can be reduced whilst still meeting the minimum requirements for essential amino acids by a judicious selection of protein sources supplemented if necessary by small quantities of free amino acids.

However, this line of development does not take account of the physiological properties of particular proteins and the evolution of protein content of human milk over time. Human milk is generally considered to be whey predominant and a range of "whey-adapted" formulas have been developed based on this. However, this fails to take account of the fact that the casein:whey ratio of human milk varies over time from 20:80 in the first few days of lactation to 50:50 after five to six months of lactation. Furthermore, the protein content of human milk is likewise not constant over time and may vary between 1.8 and 1.3 g/100 kcal depending upon the duration of lactation.

Without wishing to be bound by theory, the inventors believe that for infants at risk of developing obesity in particular, feeding a nutritional composition with a controlled protein and energy content which is moreover preferably relatively rich in the satiety-inducing protein casein could counteract any tendency on the part of the infant to overfeed, particularly as regards protein intake, whilst supplying sufficient quantities of nutrients essential for growth and development and resulting in a growth pattern similar to that observed in breast fed infants.

DETAILED DESCRIPTION OF THE INVENTION

In this specification, the following expressions have the meanings assigned to them below:—

"infant" means a child under the age of 12 months;
"infant at risk of developing obesity later in life" means an infant born to an obese mother
"normal growth rate of a breast fed infant" means the growth rates for breast fed infants set out in Acta Paediatrica, Vol 95, April 2006, Supplement 450 "WHO Child Growth Standards"
"obese mother" means a woman with a BMI greater than 30 prior to establishment of pregnancy;
"overweight mother" means a woman with a BMI greater than 25 prior to establishment of pregnancy;
"protein content" means total content of proteinaceous material including free amino acids (if present).

All percentages and ratios are by weight unless otherwise specified.

References to the energy density of the nutritional composition in a specified number of kilocalories per liter refer, in the context of powdered products, to the product after re-constitution according to the directions provided with the product.

The energy density of a nutritional composition according to the invention is less than 650 kcal/l, preferably between 620 and 640 kcal/l.

The nutritional composition of the present invention has a protein content of less than 1.8 g/100 kcal. Preferably the protein content is between 1.4 and 1.7 g/100 kcal. The detailed make-up of the protein source is not believed to be critical to the present invention provided that the minimum requirements for essential amino acid content are met and satisfactory growth is ensured. Thus, protein sources based on cows' milk proteins such as whey, casein and mixtures thereof may be used as well as protein sources based on soy. However, mixtures of whey and casein proteins are preferred. The casein:whey ratio may lie in the range from 70:30 to 30:70 but is preferably 40:60.

The protein(s) in the protein source may be intact or partially hydrolysed or a mixture of intact and hydrolysed proteins may be used. However, intact proteins are preferred.

The protein source may additionally be supplemented with free amino acids if this is necessary to meet the minimum requirements for essential amino acid content. These requirements are published for example in EC Directive 91/321/EEC. However, it will be appreciated that because of the over-riding need to control the protein content of the nutritional composition as discussed above, supplementation with free amino acids may be driven primarily by the amino acid profile of the protein source(s) selected and the resultant need to supplement with certain free amino acids if any. This is illustrated further in the examples below.

As noted above, the preferred protein source is a mixture of casein and whey proteins. The whey protein may be a whey protein isolate, acid whey, sweet whey or sweet whey from which the caseino-glycomacropeptide has been removed (modified sweet whey). Preferably, however, the whey protein is modified sweet whey. Sweet whey is a readily available by-product of cheese making and is frequently used in the manufacture of nutritional compositions based on cows' milk. However, sweet whey includes a component which is undesirably rich in threonine and poor in tryptophan called caseino-glycomacropeptide (CGMP). Removal of the CGMP from sweet whey results in a protein with a threonine content closer to that of human milk. A process for removing CGMP from sweet whey is described in EP 880902.

If modified sweet whey is used as the whey protein in a mixture of 60% whey and 40% casein, the protein source is preferably supplemented by free tryptophan, isoleucine, histidine and phenylalanine in amounts of up to 0.34% for tryptophan, 0.92% for isoleucine, 0.19% for histidine and 2.2% for phenylalanine (in each case as a percentage by weight of total protein content). If intact sweet whey is used as the whey protein in a mixture of 60% whey and 40% casein, the protein source is preferably supplemented by free tryptophan, leucine, histidine and phenylalanine in amounts of up to 0.5% for tryptophan, 0.37% for leucine, 0.3% for histidine and 2.5% for phenylalanine (in each case as a percentage by weight of total protein content).

The nutritional compositions of the present invention contains a source of carbohydrates. The preferred source of carbohydrates is lactose although other carbohydrates such as saccharose, maltodextrin, and starch may also be added. Preferably, the carbohydrate content of the nutritional composition is between 9 and 14 g/100 kcal.

The nutritional composition of the present invention contains a source of lipids. The lipid source may be any lipid or fat which is suitable for use in nutritional compositions to be fed to infants. Preferred fat sources include coconut oil, low erucic rapeseed oil (canola oil), soy lecithin, palm olein, and sunflower oil. The essential polyunsaturated fatty acids linoleic acid and α-linolenic acid will also be added as may small amounts of oils containing high quantities of pre-formed long chain polyunsaturated fatty acids arachidonic acid and docosahexaenoic acid such as fish oils or single cell oils. In total, the lipid content may be between 4.4 and 6 g/100 kcal. Preferably, the ratio of linoleic acid (C18:2n−6): α-linolenic acid (C18:3n−3) in the lipid source is less than 7:1, more preferably between 7:1 and 5:1. Further, the ratio of arachidonic acid (C20:4n−6):docosahexaenoic acid (C22: 6n−3) in the lipid source is preferably between 2:1 and 1.1.

The nutritional composition may also contain all vitamins and minerals understood to be essential in the daily diet in nutritionally significant amounts. Minimum requirements have been established for certain vitamins and minerals. Examples of minerals, vitamins and other nutrients optionally present in the nutritional composition include vitamin A, vitamin $B_1$, vitamin $B_2$, vitamin $B_6$, vitamin $B_{12}$, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form.

If necessary, the nutritional composition may contain emulsifiers and stabilisers such as soy lecithin, citric acid esters of mono- and di-glycerides, and the like. This is especially the case if the composition is provided in liquid form.

The nutritional composition may optionally contain other substances which may have a beneficial effect such as probiotic bacteria, fibres, lactoferrin, nucleotides, nucleosides, and the like in the amounts customarily found in nutritional compositions to be fed to infants.

The nutritional composition may be prepared in any suitable manner. For example, a nutritional composition may be prepared by blending together the protein source, the carbohydrate source, and the lipid source in appropriate proportions. If used, emulsifiers may be included in the blend at this stage. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled and any heat sensitive components; such as vitamins and minerals may be added. The pH and solids content of the homogenised mixture is conveniently standardised at this point.

If it is desired to produce a powdered composition, the homogenised mixture is transferred to a suitable drying apparatus such as a spray drier or freeze drier and converted to powder. The powder should have a moisture content of less than about 5% by weight.

If it is desired to produce a liquid composition, the homogenised mixture is filled into suitable containers; preferably aseptically. However, the liquid composition may also be retorted in the container. Suitable apparatus for carrying out filling of this nature is commercially available. The liquid composition may be in the form of a ready to feed composition having a solids content of about 10 to about 14% by weight or may be in the form of a concentrate; usually of solids content of about 20 to about 26% by weight.

An example of the composition of a nutritional composition according to the invention is given below:—

| Nutrient | per 100 kcal | per liter |
| --- | --- | --- |
| Energy (kcal) | 100 | 630 |
| Protein (g) | 1.5 | 9.45 |
| (skimmed milk powder, modified sweet whey) | | |
| free phenylalanine (mg) | 30 | 189 |
| free isoleucine (mg) | 13.5 | 85 |
| free tryptophan (mg) | 4.9 | 30.9 |
| free histidine (mg) | 2.5 | 15.8 |
| casein:whey ratio | 40:60 | 40:60 |
| Fat (g) | 5.3 | 33.4 |
| Linoleic acid (g) | 0.7 | 4.4 |
| α-Linolenic acid (mg) | 106 | 668 |
| DHA (mg) | 11.5 | 72.5 |
| ARA (mg) | 11.5 | 72.5 |
| Linoleic acid: α-Linolenic acid | 6.5 | 6.5 |
| Lactose (g) | 11.6 | 73.1 |
| Minerals and Electrolytes | | |
| Na (mg) | 25 | 158 |
| K (mg) | 89 | 561 |
| Cl (mg) | 64 | 403 |
| Ca (mg) | 64 | 403 |
| P (mg) | 32 | 202 |
| Ca/P | 2.0 | 2.0 |
| Mg (mg) | 6.9 | 43.5 |
| Mn (µg) | 8.0 | 50.4 |
| Vitamins and Trace Elements | | |
| Vitamin A (IU) | 350 | 2205 |
| Vitamin D (IU) | 60 | 378 |
| Vitamin E (IU) | 1.2 | 7.6 |
| Vitamin K1 (µg) | 8.0 | 50.4 |
| Vitamin C (mg) | 10 | 63 |
| Vitamin B1 (mg) | 0.07 | 0.44 |
| Vitamin B2 (mg) | 0.15 | 0.95 |
| Niacin (mg) | 1.0 | 6.3 |
| Vitamin B6 (mg) | 0.075 | 0.47 |
| Folic acid (µg) | 12 | 75.6 |
| Pantothenic acid (mg) | 0.45 | 2.83 |
| Vitamin B12 (µg) | 0.3 | 1.89 |
| Biotin (µg) | 2.2 | 13.9 |
| Choline (mg) | 10 | 63 |
| Inositol (mg) | 5.0 | 31.5 |
| Taurine (mg) | 7.0 | 44.1 |
| Carnitine (mg) | 1.6 | 10.1 |
| Fe (mg) | 1.2 | 7.56 |
| I (µg) | 15 | 94.5 |
| Cu (mg) | 0.07 | 0.44 |
| Se (µg) | 2.0 | 12.6 |
| Zn (mg) | 0.75 | 4.72 |
| Nucleotides | | |
| CMP (mg) | 2.3 | 14.5 |
| UMP (mg) | 1.5 | 9.5 |
| AMP (mg) | 0.7 | 4.4 |
| GMP (mg) | 0.3 | 1.9 |
| Probiotics | | |
| *B. lactis* CNCM I-3446 | $2 \times 10^7$ cfu/g powder | |
| *L. rhamnosus* CGMCC 1.3724 | $2 \times 10^7$ cfu/g powder | |

A nutritional composition according to the invention may be fed to an infant at risk of developing obesity later in life as the sole source of nutrition from the age of three months and subsequently as part of a mixed diet during the introduction of solid foods until weaning is complete at about the age of 12 months.

The invention claimed is:

1. A method of reducing the risk of developing obesity in an infant born to an obese or overweight mother, the method comprising:
    administering to the infant as the sole source of nutrition, from the age of three months until an introduction of solid foods, and as part of a mixed diet, from the introduction of solid foods until the age of about 12 months, a composition comprising a protein source that includes at least 20% by weight casein, a lipid source having a ratio of linoleic acid (C18:2n-6):α-linolenic acid (C18:3n-3) between 7:1 and 5:1, a carbohydrate source, a protein content between 1.4 and 1.7 g/100 kcal, a probiotic bacterial strain selected from the group consisting of *B. lactis, L. rhamnosus* and a combination thereof, in an amount of from $10^6$ to $10^{11}$ cfu/g of composition (dry weight), and an energy density of less than 650 kcal/liter.

2. The method of claim 1, wherein the energy density of the composition is between 620 and 640 kcal/liter.

3. The method of claim 1, wherein the protein source includes whey protein.

4. The method of claim 1, wherein the ratio of casein:whey is between 30:70 and 70:30.

5. The method of claim 3, wherein the whey protein is sweet whey from which the caseino-glycomacropeptide has been removed.

6. The method of claim 1, wherein the protein(s) are intact.

7. The method of claim 1, wherein the carbohydrate source is lactose and an additional carbohydrate selected from the group consisting of saccharose, maltodextrin, starch and combinations thereof.

8. A method of reducing the risk of obesity and promoting a rate of growth in an infant born to an obese or overweight mother, the promoted rate of growth approximates the rate of growth of a breast fed infant of the same age, the method comprising:

administering to the infant as the sole source of nutrition, from the age of three months until an introduction of solid foods, and as part of a mixed diet, from the introduction of solid foods until the age of about 12 months, a composition comprising a protein source, a lipid source having a ratio of linoleic acid (C18:2n–6): α-linolenic acid (C18:3n–3) between 7:1 and 5:1, a carbohydrate source, a protein content between 1.4 and 1.7 g/100 kcal, a probiotic bacterial strain selected from the group consisting of *B. lactis, L. rhamnosus* and a combination thereof, in an amount of from $10^6$ to $10^{11}$ cfu/g of composition (dry weight), and an energy density of less than 650 kcal/liter.

9. The method of claim 8, wherein the energy density of the composition is between 620 and 640 kcal/liter.

10. The method of claim 8, wherein the protein source includes whey protein.

11. The method of claim 8, wherein the ratio of casein:whey is between 30:70 and 70:30.

12. The method of claim 10, wherein the whey protein is sweet whey from which the caseino-glycomacropeptide has been removed.

13. The method of claim 8, wherein the protein is intact.

14. The method of claim 8, wherein the carbohydrate source is lactose.

15. The method of claim 14, wherein the composition comprises an additional carbohydrate selected from the group consisting of saccharose, maltodextrin, starch and combinations thereof.

* * * * *